United States Patent
Huo et al.

(10) Patent No.: US 10,383,813 B2
(45) Date of Patent: Aug. 20, 2019

(54) SKIN LIGHTENING COSMETIC COMPOSITION AND PREPARATION METHOD THEREOF

(71) Applicant: OSM Biology Co., Ltd., Zhejiang (CN)

(72) Inventors: Gang Huo, Zhejiang (CN); Xueyang Deng, Zhejiang (CN); Ping Ma, Zhejiang (CN)

(73) Assignee: OSM Biology Co., Ltd., Zhejiang (CN)

(*) Notice: Subject to any disclaimer, the term of this patent is extended or adjusted under 35 U.S.C. 154(b) by 7 days.

(21) Appl. No.: 15/558,567

(22) PCT Filed: Oct. 28, 2015

(86) PCT No.: PCT/CN2015/093021
§ 371 (c)(1),
(2) Date: Sep. 15, 2017

(87) PCT Pub. No.: WO2016/145859
PCT Pub. Date: Sep. 22, 2016

(65) Prior Publication Data
US 2018/0055762 A1    Mar. 1, 2018

(30) Foreign Application Priority Data
Mar. 17, 2015 (CN) .......................... 2015 1 0116273

(51) Int. Cl.
| *A61Q 19/02* | (2006.01) |
| *A61K 8/34* | (2006.01) |
| *A61K 8/64* | (2006.01) |
| *A61K 8/73* | (2006.01) |
| *A61K 8/9789* | (2017.01) |
| *A61K 8/98* | (2006.01) |
| *A61K 8/97* | (2017.01) |

(52) U.S. Cl.
CPC .............. *A61K 8/987* (2013.01); *A61K 8/345* (2013.01); *A61K 8/64* (2013.01); *A61K 8/738* (2013.01); *A61K 8/97* (2013.01); *A61K 8/9789* (2017.08); *A61K 8/98* (2013.01); *A61Q 19/02* (2013.01)

(58) Field of Classification Search
None
See application file for complete search history.

(56) References Cited

U.S. PATENT DOCUMENTS 7,820,211 B2 * 10/2010 Hitomi ..................... A61K 8/97
424/400

FOREIGN PATENT DOCUMENTS

| CN | 104042547 | 9/2014 |
| JP | 2004123563 | 4/2004 |

OTHER PUBLICATIONS

"International Search Report (Form PCT/ISA/210)", dated Feb. 3, 2016, with English translation thereof, pp. 1-4.

* cited by examiner

*Primary Examiner* — Zohreh A Fay
(74) *Attorney, Agent, or Firm* — JCIPRNET

(57) ABSTRACT

A cosmetic composition for whitening skin and a preparation method thereof. The composition comprises the following components: pearl powder, pearl extract, glycyrrhiza glabra aqueous solution, hydrolyzed conchiolin protein and pea extract. The contents of the pearl powder and the pearl extract are not both zero, and the glycyrrhiza glabra aqueous solution contains 0.5 to 5.0% of the glycyrrhiza glabra extract.

13 Claims, 1 Drawing Sheet

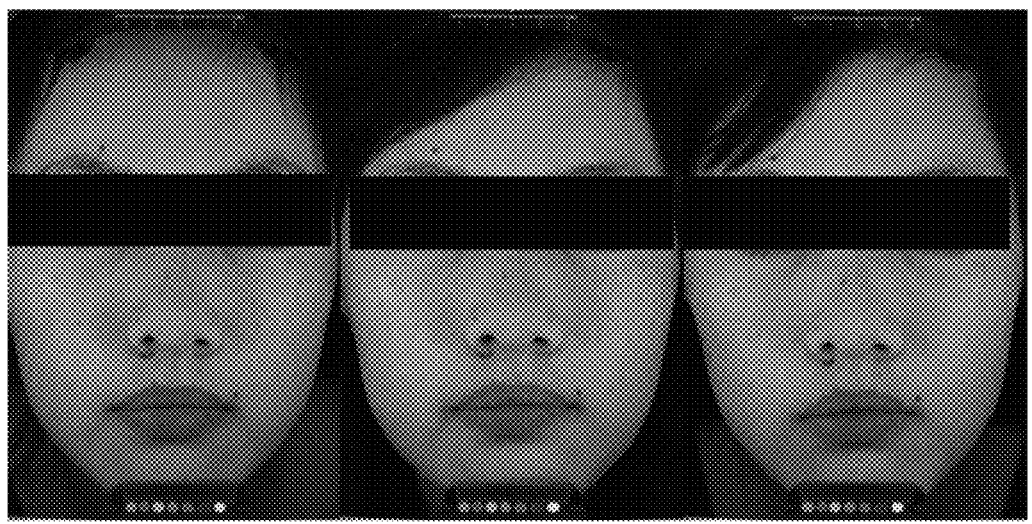

SKIN LIGHTENING COSMETIC COMPOSITION AND PREPARATION METHOD THEREOF

CROSS-REFERENCE TO RELATED APPLICATION

This application is a 371 of international application of PCT application serial no. PCT/CN2015/093021, filed on Oct. 28, 2015, which claims the priority benefit of China application no. 201510116273.7, filed on Mar. 17, 2015. The entirety of each of the above-mentioned patent applications is hereby incorporated by reference herein and made a part of this specification.

BACKGROUND OF THE INVENTION

1. Field of the Invention

The present invention generally relates to cosmetic field. In particular, it relates to a skin lightening cosmetic composition and a preparation method thereof.

2. Description of Related Art

The colors of human skin, hair and eyes are mainly related to the type, quantity and distribution of melanin synthesized by the melanocyte. In the melanocytes, tyrosine has been oxidized into dopa and dopaquinone by the catalysis of the tyrosinase, and the dopaquinone is further converted to dopa pigment. Then, the dopa pigment is further converted to 5,6-indole quinone and 5,6-indole quinone-2-carboxylic acid via 5,6-dihydroxyindole and 5,6-dihydroxyindole-2-carboxylic acid by the catalysis of the DHI enzyme as well as dopa pigment enzyme and DHICA oxidase, respectively. Finally, the 5,6-indole quinone and 5,6-indolequinone-2-carboxylic acid are polymerized to form melanin. Tyrosinase is the rate-limiting enzyme and key enzyme in the first step of the melanin synthesis, thus, most lightening agents contain tyrosinase inhibitors.

Human epidermal basal cells contain 4%~5% pigment cells. The color of human skin does not depend on the number of melanocytes, but on the number, size, distribution and melanization of melanosome. Therefore, some lightening ingredients achieve the lightening effect by affecting the formation, maturation and transfer of melanosome.

Keratinocytes will release endothelin under the ultraviolet radiation. The endothelin binding to the receptors on the melanoma cell membrane stimulates the proliferation of the melanocytes, activates the tyrosinase activity, accelerates the growth of dendritic protrusions of melanocytes, and accelerates the synthesis of melanin and the migration of melanin to keratinocytes. Therefore, in order to effectively inhibit the blackening effect of the keratinocytes on the skin, it is essential to block the keratinocytes transferring information to melanoma cells. In present, endothelin antagonists have gradually become a class of important lightening agents.

As the reasons for the formation of melanin are multifaceted, only fully considering the reasons of the formation of melanin, efficient lightening products can be designed. However, owing to the multi-channel effect on the formation and transfer of melanin, we must take the safety, stability and appearance of the product into account. Therefore, it has great significance of choosing a multi-functional, stable, safe, and light color lightening raw materials which is playing synergistic lightening effect.

SUMMARY

The present invention collectively considers various factors for the formation of melanin. Thus, an object of the present invention is to provide a skin lightening composition of which the major active ingredient is biological enzymolysis products of a plurality of natural extracts and natural extracts. These biological enzymolysis products act synergistically to suppress the production and migration of the melanin, finally achieving the effect of lightening skin. Another object of the present invention is to provide a preparation method of the skin lightening composition above.

The present invention provides a skin lightening cosmetic composition, and the composition is calculated by weight percentage. The composition comprises:
  0 to 30% pearl powder;
  0 to 10% pearl extract;
  0.1 to 10% glycyrrhiza glabra aqueous solution;
  0.005 to 1% hydrolyzed conchiolin protein;
  0.1 to 5% pea extract.
wherein the content of the pearl powder and the pearl extract is not zero at the same time, and the percentage of the glycyrrhiza glabra extract in the glycyrrhiza glabra aqueous solution is 0.5 to 5.0%.

As a preferred embodiment, the skin lightening cosmetic composition based on weight percentage comprises:
  0.5 to 20% pearl powder;
  0.5 to 5% pearl extract;
  0.3 to 3% glycyrrhiza glabra aqueous solution;
  0.01 to 0.3% hydrolyzed conchiolin protein;
  0.5 to 3% pea extract.

As a preferred embodiment, the skin lightening cosmetic composition based on weight percentage comprises:
  1.0 to 15% pearl powder;
  1.0 to 4% pearl extract;
  0.5 to 3% glycyrrhiza glabra aqueous solution;
  0.05 to 0.2% hydrolyzed conchiolin protein;
  1.0 to 2.5% pea extract.

As a preferred embodiment the percentage of the glycyrrhiza glabra extract in the glycyrrhiza glabra aqueous solution is 1.0 to 3.0%.

As a preferred embodiment, the glycyrrhiza glabra aqueous solution is synthesized by the following steps. The glycyrrhiza glabra extract is dispersed in water after enveloped by the hydroxypropyl cyclodextrin, then the 1,2-pentadiol is added into the above solution. The weight fraction of glabridin in the extract of glycyrrhiza glabra was more than 90%.

As a preferred embodiment, the pearl powder is 1,000 to 3,000 mesh powder obtained by physical mechanical grinding of pearls.

As a preferred embodiment, the pearl extract is a mixture of a plurality of peptides and amino acids obtained by the enzymolysis of pearl powder.

As a preferred embodiment, the hydrolyzed conchiolin protein is a powdery substance obtained by biological enzymolysis of conchiolin of aquatic organism, and its weight purity is more than 70%.

As a preferred embodiment, the weight purity of pea extract is 2~3%.

Beneficial Effect

The pearl powder in the skin lightening composition is a good nutritious ingredient for the human skin. It can not only improve the barrier function of the skin, but also moisturizing the skin and increasing the hydration of the skin and inhibiting the activity of tyrosinase remarkably. In addition, the studies have shown that the pearl powder has a strong ability to inhibit and remove free radicals.

The pearl extract in the skin lightening composition contains pearl native polypeptide and a variety of essential amino acids. The pearl native polypeptide could inhibit endothelin from activating tyrosinase and promoting melanocyte differentiation. The amino acid can promote the growth of skin cells, inhibit tyrosinase from promoting the formation of melanin activity, and eliminate free radicals etc.

The glabridin having significant anti-inflammatory and lightening effect is the active ingredients of glycyrrhiza glabra aqueous solution in the skin lightening composition. It is one of the approved, safest, most effective lightening ingredients published internationally and recognized as the white gold in the industry, while it only exists in the roots of the glycyrrhiza glabra. However, in the application, it was found that the low-purity glabridin has a color, deepened under a high temperature condition, which has an adverse effect on the color of cosmetics. In the present invention, as the content of the glycyrrhiza glabra extract was not less than 90%, the color of the cosmetics was less affected in the use. In addition, after enveloped by the hydroxypropyl cyclodextrin, the glycyrrhiza glabra extract is dissolved into water to form aqueous solution which is convenient to use.

In the skin lightening composition, the hydrolyzed conchiolin protein is an endothelin antagonist which is a natural lightening additive extracted, isolated and purified from natural products. In the mid-90s, skin physiologists have found that after human skin is exposed to ultraviolet light (UVB), the keratinocytes release endothelin. When the endothelin information is accepted by receptors on the melanoma cell membrane, the differentiation and proliferating of melanocytes were stimulated and tyrosinase activity was activated, thereby there is a sharp increase of melanin. Endothelin antagonists can preferentially bind to the receptors of the melanocytic cell membrane to render endothelin ineffective, so that it can inhibit the proliferation of melanocytes and the synthesis of melanin caused by the release of endothelin due to UV radiation, and inhibit the release of endothelial cells by keratinocytes. Thererby, it is a safe and efficient lightening agent which plays a lightening effect.

The pea extract in the skin lightening composition inhibits the activity of the Pmel 17 protein gene, while Pmel 17 is the key gene for the maturation of melanosome. This can reduce the generation of melanin from the source, and has the effect of lightening and lighten pigmentation.

BRIEF DESCRIPTION OF THE DRAWINGS

FIG. 1 is a graph of the subjects' appearance.

DESCRIPTION OF THE EMBODIMENTS

The present invention also discloses a lightening cosmetic product comprising the above-mentioned skin lightening cosmetic composition, common base for cosmetic external dosage, and water.

The skin lightening cosmetic composition provided in the present invention comprises pearl powder or pearl extract, glycyrrhiza glabra aqueous solution, hydrolyzed conchiolin protein and pea extract as the main components, and emulsifier, skin care, moisturizers, thickeners, preservatives, flavors and water in a cosmetic common base component as supplement. The present invention is discussed in further detail in the following sections, but this is not limited to the invention.

Example I

The Skin Lightening Composition

The skin lightening composition comprises the components and their percentage as follows:

| | |
|---|---|
| glycerin | 5 |
| xanthan gum | 0.1 |
| pearl extract | 2 |
| glycyrrhiza glabra aqueous solution | 2 |
| hydrolyzed conchiolin protein | 0.05 |
| pea extract | 1 |
| preservative | 0.8 |
| water | margin |

The procedure for preparing the skin lightening composition in the above table included the following steps. The water, glycerin and xanthan gum were added in a reaction kettle, and the resulting mixture was stirred and heated to a temperature of 75-80° C. Then, the mixture was cooled down to 45-50° C. by stirring with the cooling circulation system, and followed by addition of the pearl extract, glycyrrhiza glabra aqueous solution, hydrolyzed conchiolin protein, pea extract and preservative. The resulting mixture was stirred and dissolved completely. Subsequently, the mixture was stirred and cooled to a temperature below 38° C. The stirring was stopped to end.

Example II

Lightening Essence

The lightening essence for lightening skin comprise the components and their percentage as follows:

| | |
|---|---|
| glycerin | 8 |
| ammonium acryloyl dimethyl taurate/VP copolymer | 0.5 |
| xanthan gum | 0.1 |
| sodium hyaluronate | 0.05 |
| pearl extract | 5 |
| glycyrrhiza glabra aqueous solution | 3 |
| hydrolyzed conchiolin protein | 0.2 |
| pea extract | 3 |
| essence | 0.05 |
| preservative | 0.8 |
| water | margin |

The procedure for preparing the lightening essence in the above table included the following steps. The water, glycerin, ammonium acryloyl dimethyl taurate/VP copolymer, xanthan gum and sodium hyaluronate were added in a reaction kettle, and the resulting mixture was stirred and heated to a temperature of 75-80° C. and then dispersed evenly. Then, the mixture was cooled down to 45-50° C. with stirring with the cooling circulation system, followed by addition of the pearl extract, glycyrrhiza glabra aqueous solution, hydrolyzed conchiolin protein, pea extract, essence and preservative. The mixture was homogenized for 1 min, and stirred to be dissolved completely. Subsequently, the mixture was stirred and cooled to a temperature below 38° C. The stirring was stopped to end.

Example III

Lightening Cream 1

The lightening cream 1 for lightening skin comprises the components and their percentage as follows:

| | |
|---|---|
| magnesium aluminum silicate | 1 |
| potassium cetyl phosphate | 0.3 |
| nicotinamide | 2 |
| biological buffers | 1 |
| pearl powder | 20 |
| 1,3-propanediol | 10 |
| xanthan gum | 0.3 |
| cetearyl alcohol | 3 |
| isohexadecanol | 2 |
| shea butter | 1 |
| polydimethylsiloxane | 2 |
| caprylic/capric triglyceride | 5 |
| methyl glucose sesquistearate | 1 |
| PEG-20 methyl glucosyl sesquiostearate | 2 |
| glycyrrhiza glabra aqueous solution | 2 |
| hydrolyzed conchiolin protein | 0.09 |
| pea extract | 2 |
| essence | 0.2 |
| preservative | 0.8 |
| water | Margin |

The procedure for preparing the lightening cream 1 in the above table included the following steps. The magnesium aluminum silicate, potassium cetyl phosphate, nicotinamide, biological buffers and water were added into a water pan and heated to a temperature of 75-80° C. with stirring, and the mixture was homogenized for 5 min as phase A. Then the pearl powder, 1,3-propanediol and xanthan gum were mixed and dispersed as phase B. The phase B was added to the phase A, and the resulting mixture was heated to 75-80° C., stirred and dispersed evenly. The cetearyl alcohol, isohexadecanol, shea butter, polydimethylsiloxane, caprylic/capric triglyceride, methyl glucose sesquistearate, and PEG-20 methyl glucosyl sesquiostearate were added to the oil pan, and the mixture was heated to 80-85° C., stirred and dissolved completely as phase C. The phase A and phase B were pumped into a homogeneous reaction pot with stirring, then the phase C was pumped therein. Next, the mixture was homogenized for 5 minutes. The cooling circulation water was opened. The mixture was stirred and cooled to a temperature of 45-50° C. The glycyrrhiza glabra aqueous solution, hydrolyzed conchiolin protein, pea extract, essence and preservative were added. The mixture was stirred to be dissolved completely. Subsequently, the mixture was stirred and cooled to a temperature below 38° C. The stirring was stopped to end.

Example IV

Lightening Cream 2

The lightening cream 2 for lightening skin comprise the component as follows and their percentage:

| | |
|---|---|
| glycerin | 8 |
| lecithin | 1 |
| C12-16 alcohol | 2 |
| palmitic acid | 1 |
| pearl powder | 0.5 |
| butanediol | 5 |
| polyglutamic acid | 0.05 |
| cetearyl alcohol | 3 |
| virgin olive oil | 2 |
| shea butter | 1 |
| polydimethylsiloxane | 3 |
| caprylic/capric triglyceride | 3 |
| cetearyl ethylhexanoate | 5 |
| glycyrrhiza glabra aqueous solution | 1 |
| hydrolyzed conchiolin protein | 0.03 |
| pea extract | 2 |
| essence | 0.2 |
| preservative | 0.8 |
| water | margin |

The procedure for preparing the lightening cream 2 in the above table included the following steps. The glycerin, lecithin, C12-16 alcohol, palmitic acid and water were added into a water pan. The mixture was heated to a temperature of 75-80° C., and stirred for 30 min as phase A. Then the pearl powder, butanediol and polyglutamic acid were mixed and dispersed as phase B. The phase B was added to the phase A, and the resulting mixture was heated to 75-80° C., stirred and dispersed evenly. The cetearyl alcohol, virgin olive oil, shea butter, polydimethylsiloxane, caprylic/capric triglyceride, cetearyl ethylhexanoate were added to the oil pan, and the mixture was heated to 80-85° C., stirred and dissolved completely as phase C. The phase A and phase B were pumped into the homogeneous reaction pot with stirring, then the phase C was pumped therein. Next, the mixture was homogenized for 5 minutes. The cooling circulation water was opened. The mixture was stirred and cooled to a temperature of 45-50° C. The glycyrrhiza glabra aqueous solution, hydrolyzed conchiolin protein, pea extract, essence and preservative were added. The mixture was stirred to be dissolved completely. Subsequently, the mixture was stirred and cooled to a temperature below 38° C. The stirring was stopped to end.

Example V: The Evaluation of Lightening Effect

In this experiment, the lightening cream 2 provided in example 4 was subjected to clinical trials.

The experiment included 23 female volunteers aged 23-50 years old, and there was facial pigmentation caused by the sun, working pressure, and age. During the trial, the test substance was used according to the provisions and the information was complete. The lightening cream 2 was applied twice a day (morning and evening), and the test period was 4 weeks. Facial image data was obtained via VISIA-CR at W0 (before using), W2 (using 2 weeks), W4 (using 4 weeks), respectively, and the change of L* value of face specific stains was analysed with SSA software. In addition, the t test was used to test the difference. The results are as follows:

| 1. Table of L value change | | | | |
|---|---|---|---|---|
| Index | Time | Mean ± standard deviation | t value | P value |
| L value | W0 | 53.5302 ± 5.13340 | | |
| | W2 | 54.6884 ± 5.55446 | 4.992 | 0.000** |
| | W4 | 55.3170 ± 5.39473 | 7.589 | 0.000** |

**means that the difference is very significant ($P < 0.01$)

From the table, we can see that there was an increasing trend of the skin color L* value after using the lightening cream 2 for two weeks, and it was significantly greater than the level before using. The difference was statistically significant ($p<0.01$) which indicated that the skin color had gradually shallowed and the stains gradually had faded after using the lightening cream on face.

As can be seen from FIG. 1, the facial skin color had brightened obviously at the W2, and the effect have been maintained very well at the W4, which is consistent with the L value of the face.

2. the Self-Evaluation of Volunteers

By adopting questionnaire survey method, the subjects were mobilised to evaluate the degree of skin improvement by self-assessing the skin color depth and the changes of the stains size before and after using the product. No improvement means there was no change in the size of the stains and no change in skin color. The mild improvement means the stains have shrunk down and faded slightly, and the overall skin color was brightened. The moderate improvement means the stains have shrunk down and faded significantly, and the overall skin color was brightened obviously. Within the four weeks using the sample, the subjects considered that the women who received the moderate improvement of the facial skin occupied the total number of 38%, and the mild improvement accounting for 54%. In terms of the stains improvement, the women who received he moderate improvement occupied the total number of 15%, while the mild improvement accounting for 77%.

In summary, the lightening product has a significant whitening effect, that is the dual effect including brightening skin color and diluting the stains.

What is claimed is:

1. A skin lightening cosmetic composition, comprising:
   0 to 30 wt % pearl powder;
   0 to 10 wt % pearl extract, wherein the pearl extract is a mixture of a plurality of peptides and amino acids obtained by enzymolysis of pearl powder, and the content of the pearl powder and the pearl extract is not zero at the same time;
   0.1 to 10 wt % glycyrrhiza glabra aqueous solution, wherein the glycyrrhiza glabra aqueous solution contains 0.5 to 5.0 wt % glycyrrhiza glabra extract and is formed by the following steps:
      enveloping the glycyrrhiza glabra extract by hydroxypropyl cyclodextrin, wherein the glycyrrhiza glabra extract contains more than 90 wt % of hydrophobic glabridin;
      dispersing the enveloped glycyrrhiza glabra extract into water to form a dispersion; and
      adding 1, 2-pentadiol to the dispersion;
   0.005 to 1 wt % hydrolyzed conchiolin protein, wherein the hydrolyzed conchiolin protein is a powdery substance obtained by biological enzymolysis of conchiolin of aquatic organism, and its weight purity is more than 70 wt %; and
   0.1 to 5 wt % pea extract.

2. The skin lightening cosmetic composition of claim 1, wherein the composition comprises:
   0.5 to 20 wt % pearl powder;
   0.5 to 5 wt % pearl extract;
   0.3 to 3 wt % glycyrrhiza glabra aqueous solution;
   0.01 to 0.3 wt % hydrolyzed conchiolin protein; and
   0.5 to 3 wt % pea extract.

3. The skin lightening cosmetic composition of claim 1, wherein the composition comprises:
   1.0 to 15 wt % pearl powder;
   1.0 to 4 wt % pearl extract;
   0.5 to 3 wt % glycyrrhiza glabra aqueous solution;
   0.05 to 0.2 wt % hydrolyzed conchiolin protein; and
   1.0 to 2.5 wt % pea extract.

4. The skin lightening cosmetic composition of claim 1, wherein the glycyrrhiza glabra aqueous solution contains 1.0 to 3.0 wt % glycyrrhiza glabra extract.

5. The skin lightening cosmetic composition of claim 4, wherein the composition comprises:
   0.5 to 20 wt % pearl powder;
   0.5 to 5 wt % pearl extract;
   0.3 to 3 wt % glycyrrhiza glabra aqueous solution;
   0.01 to 0.3 wt % hydrolyzed conchiolin protein; and
   0.5 to 3 wt % pea extract.

6. The skin lightening cosmetic composition of claim 4, wherein the composition comprises:
   1.0 to 15 wt % pearl powder;
   1.0 to 4 wt % pearl extract;
   0.5 to 3 wt % glycyrrhiza glabra aqueous solution;
   0.05 to 0.2 wt % hydrolyzed conchiolin protein; and
   1.0 to 2.5 wt % pea extract.

7. The skin lightening cosmetic composition of claim 1, wherein the pearl powder is 1,000 to 3,000 mesh powder obtained by physical mechanical grinding of pearls.

8. The skin lightening cosmetic composition of claim 7, wherein the composition comprises:
   0.5 to 20 wt % pearl powder;
   0.5 to 5 wt % pearl extract;
   0.3 to 3 wt % glycyrrhiza glabra aqueous solution;
   0.01 to 0.3 wt % hydrolyzed conchiolin protein; and
   0.5 to 3 wt % pea extract.

9. The skin lightening cosmetic composition of claim 7, wherein the composition comprises:
   1.0 to 15 wt % pearl powder;
   1.0 to 4 wt % pearl extract;
   0.5 to 3 wt % glycyrrhiza glabra aqueous solution;
   0.05 to 0.2 wt % hydrolyzed conchiolin protein; and
   1.0 to 2.5 wt % pea extract.

10. The skin lightening cosmetic composition of claim 1, wherein a weight purity of the pea extract is 2 to 3 wt %.

11. The skin lightening cosmetic composition of claim 10, wherein the composition comprises:
   0.5 to 20 wt % pearl powder;
   0.5 to 5 wt % pearl extract;
   0.3 to 3 wt % glycyrrhiza glabra aqueous solution;
   0.01 to 0.3 wt % hydrolyzed conchiolin protein; and
   0.5 to 3 wt % pea extract.

12. The skin lightening cosmetic composition of claim 10, wherein the composition comprises:
   1.0 to 15 wt % pearl powder;
   1.0 to 4 wt % pearl extract;
   0.5 to 3 wt % glycyrrhiza glabra aqueous solution;
   0.05 to 0.2 wt % hydrolyzed conchiolin protein; and
   1.0 to 2.5 wt % pea extract.

13. A lightening cosmetic product, comprising:
   the skin lightening cosmetic composition of claim 1;
   a common base for cosmetic external dosage; and
   water.

* * * * *